United States Patent
Meredith

(10) Patent No.: US 10,251,975 B2
(45) Date of Patent: Apr. 9, 2019

(54) SURFACE TREATMENT PROCESS FOR IMPLANTABLE MEDICAL DEVICE

(75) Inventor: Neil Meredith, Brisbane (AU)

(73) Assignee: NEOSS LIMITED, Harrogate, Yorkshire (GB)

( * ) Notice: Subject to any disclaimer, the term of this patent is extended or adjusted under 35 U.S.C. 154(b) by 359 days.

(21) Appl. No.: 13/202,316

(22) PCT Filed: Feb. 19, 2010

(86) PCT No.: PCT/GB2010/050285
§ 371 (c)(1),
(2), (4) Date: Oct. 14, 2011

(87) PCT Pub. No.: WO2010/094968
PCT Pub. Date: Aug. 26, 2010

(65) Prior Publication Data
US 2012/0040102 A1 Feb. 16, 2012

(30) Foreign Application Priority Data
Feb. 19, 2009 (GB) .................... 0902705.3

(51) Int. Cl.
*A61L 27/30* (2006.01)
*A61L 27/50* (2006.01)

(52) U.S. Cl.
CPC ............... *A61L 27/30* (2013.01); *A61L 27/50* (2013.01); *A61L 2400/18* (2013.01)

(58) Field of Classification Search
CPC .................................. A61C 8/00; A61F 2/06
USPC .............. 523/105; 427/2.27, 2.26; 433/201.1
See application file for complete search history.

(56) References Cited

U.S. PATENT DOCUMENTS

| | | |
|---|---|---|
| 5,798,146 A | 8/1998 | Murokh et al. |
| 5,876,453 A | 3/1999 | Beaty |
| 2002/0143398 A1 | 10/2002 | Osaka et al. |
| 2004/0054422 A1 | 3/2004 | Descouts et al. |
| 2004/0121290 A1* | 6/2004 | Minevski ............. A61C 8/0012 433/201.1 |
| 2005/0165128 A1* | 7/2005 | Cohn et al. ................... 523/105 |
| 2006/0052744 A1 | 3/2006 | Weber |
| 2007/0225800 A1* | 9/2007 | Sahatjian et al. ............ 623/1.42 |
| 2007/0299535 A1 | 12/2007 | Ihde |
| 2008/0241353 A1* | 10/2008 | Liu ............................. 427/2.27 |

FOREIGN PATENT DOCUMENTS

| | | |
|---|---|---|
| EP | 0987031 A1 | 3/2000 |
| EP | 1825828 A1 | 8/2007 |

(Continued)

OTHER PUBLICATIONS

Unknown, Anodizing, Jan. 2008, Wikipedia, http://web.archive.org/web/20080110200558/http://en.wikipedia.org/wiki/anodizing.*

(Continued)

*Primary Examiner* — Andrew J Bowman
(74) *Attorney, Agent, or Firm* — Alleman Hall Creasman & Tuttle LLP

(57) ABSTRACT

A surface treatment process for an implantable medical device including a surface dielectric insulating layer, the process comprising the application of ions onto said dielectric insulating layer, the ions being capable of forming an electrostatic charge and locally creating an electric field associated with at least part of the surface of said implantable medical device upon application of a liquid to said surface.

31 Claims, 2 Drawing Sheets

(56) References Cited

FOREIGN PATENT DOCUMENTS

| EP | 1847278 | A1 | | 10/2007 | | |
|---|---|---|---|---|---|---|
| EP | 1872805 | A2 | | 1/2008 | | |
| EP | 2014319 | | * | 1/2009 | ............. | A61L 27/06 |
| EP | 2014319 | A1 | * | 1/2009 | ............. | A61L 27/30 |
| EP | 2014319 | A1 | | 1/2009 | | |
| WO | 03086495 | A1 | | 10/2003 | | |
| WO | 2005088388 | A1 | | 9/2005 | | |
| WO | WO2005/084577 | | * | 9/2005 | ............. | A61C 8/00 |
| WO | 2007107589 | A1 | | 9/2007 | | |
| WO | 2008098976 | A2 | | 8/2008 | | |
| WO | 2008127224 | A1 | | 10/2008 | | |
| WO | 2009007371 | A1 | | 1/2009 | | |
| WO | 2009097218 | A1 | | 8/2009 | | |

OTHER PUBLICATIONS

Unnkown, Magnesium chloride, Wikipedia, pp. 1-8.*

Eliaz et al., "The Effect of Surface Treatment on the Surface Texture and Contact Angle of Electrochemically Deposited Hydroxyapatite Coating and on its Interaction with Bone-Forming Cells", Acta Biomaterialia, vol. 5, No. 8, Apr. 10, 2009, pp. 3178-3191.

Molenberg, A. et al., "Improved Osseointegration of a Novel, Hydrophilic Ti Surface—a Review," Materialwissenschaft and Werkstofftechnik, vol. 40, Jan. 2009, 6 pages.

Rupp, F. et al., "Enhancing Surface Free Energy and Hydrophilicity through Chemical Modification of Microstructured Titanium Implant Surfaces," Wiley InterScience, Wiley Periodicals, Inc., Nov. 3, 2005, 12 pages.

Mugele, F. et al., "Electrowetting: from basics to applications," Journal of Physics: Condensed Matter, vol. 17, No. 28, Jul. 1, 2005, 70 pages.

Intellectual Property Office of Great Britain, Search Report Issued in Application No. 0902705.3, Jul. 30, 2009, 5 pages.

Diviniti, N., "Test report—Wettability using MgCl," NEOSS Document No. 10906, Prepared May 28, 2009, Published Apr. 29, 2015, 4 pages.

Diviniti, N., "Representation of Data from Test Report—Wettability using MgCl," Published Apr. 29, 2015, 1 page.

Engman, F., "Visual effect on implant being exposed to NaCl vs MgCl," NEOSS Report 20150419, Published Apr. 29, 2015, 1 page.

* cited by examiner

SURFACE TREATMENT PROCESS FOR IMPLANTABLE MEDICAL DEVICE

This invention relates to the field of surface treatment processes for implantable medical devices and medical devices treated with such processes.

BACKGROUND

In many types of implanted medical device (for example, orthopedic implants, pedicle screws, dental implants, spinal implants and sensors) it is desirable to have a strong interaction between the surface of the device and the surrounding tissues (most commonly bone) for the purpose of load and stress transmission. Such devices are used to stabilize fractures, strengthen weak bones and anchor prostheses.

The surfaces of such devices (hereafter referred to generally as "implants") have been shown to osseointegrate when surrounded by bone. Osseointegration (the formation of a structural connection between the implant and the surrounding living bone) occurs following implant placement as a result of new bone formation or remodelling of the existing bone which is in direct contact with the implant's surface. Bone may form directly onto the implant surface or there may be a very thin interposed protein layer. Such osseointegration has been demonstrated in many studies histologically, radiographically and with pull out, removal torque, resonance frequency analysis and other mechanical tests.

Implants are typically pure metals, alloys or ceramic devices. Titanium, zirconia, hafnium, tantalum, stainless steel and cobalt chromium are commonly used materials. It is well understood that the surface topography (roughness, surface characterization whether random or repeated) of the implant may influence the rate and quality of bone formation at the implant-tissue interface. In general, it is considered that implants which have been roughened on the nanometer and micrometer scale can increase the rate and quality of bone formation. The consequent reduction in the time taken for healing and osseointegration is highly desirable, enabling early loading and reduced treatment times. In addition the strength and stiffness of the implant-bone interface can be greater with surfaces having certain topographies.

There are a number of well documented methods for the alteration of the surface topography or roughness of implants. These may include particle blasting (grit, sand and other abrasive particles), acid etching, plasma spraying, anodizing, micro-arc oxidation or a combination of these. This may result in a single level of roughness or multiple modulated levels of roughness ranging from a scale of 1 nm to 100 µm. Topography and textures of these types are well known from commercial products and for example from EP 0 388 576.

The surface modification processes described above can also alter the chemistry of the surface. Typically metals form surface oxides on exposure to air and water. Such exposure may occur during production or surgical placement or handling. A reaction with water can occur on the implant surface wherein hydroxyl groups form (Boehm H. P., 1971 Acidic and basic properties of hydroxylated metal oxide surfaces, Discussions of the Faraday Society, 52, 264-275). Chemically, the surface of the implant may be the metal itself, an oxide of the metal, or a hydroxylated surface, for example titanium, titanium oxide or titanium hydroxyl. Carbon and other impurities may be present on the implant surface as a result of the production, storage or handling procedures.

It is highly desirable that, when an implant is placed into the tissues or bone, it is thoroughly wetted with the body's natural tissue fluids. Tissue fluids contain nutrients, electrolytes, proteins, growth factors and other substances essential in the healing and bone formation process. Implants may also be pre-treated with liquids or gels, growth factors for example during production or prior to treatment. Any liquid, gel or solution contacting an implant should thoroughly wet the surface and penetrate any topographical features.

It has been shown that there is a correlation between biocompatibility, bioadhesion and surface tension or contact angle on a substrate or implant surface (Baier, 1972, The role of surface energy in thrombogenesis, Bull. N.Y. Acad. Med. 48, 257-272). One of the major problems with implants having roughened surfaces is the potential hydrophobicity or inability of the surface to wet adequately when liquids are applied to it. This may be due to contamination of the surface with organic or hydrophobic material or to the geometry of the surface preventing penetration of fluid due to surface tension. Wetting, hydrophilicity and hydrophobicity of surfaces measured as the contact angle can readily be deduced using a goniometer or Wihelmy plate.

It is essential that tissue fluids or applied liquids penetrate the topography of a surface completely to ensure that nutrients, proteins and growth factors can maintain cell metabolism, healing and bone formation. However the nature of the topography or texture of the surface is important. Increasing the roughness of a surface may cause air to be trapped under a liquid layer preventing wetting. In addition, the aspect ratio (height or depth of troughs or porosities in relation to their width or circumference) of the topography is critical as this may cause bridging and bridge formation with a failure of a fluid to penetrate such features.

It is therefore an object of the present invention to provide a method of treating an implant whereby the hydrophilicity or wetting of an implant surface may be increased to increase the penetration of liquids onto the surface. Alternatively, or in addition, specific biomolecules could be attracted to the surface. These objects may be achieved over part or the entirety of the implant's surface.

SUMMARY OF THE DISCLOSURE

In accordance with a first aspect of the present invention there is provided a surface treatment process for an implantable medical device including a surface dielectric insulating layer, the process comprising the application of ions onto said dielectric insulating layer, the ions being capable of forming an electrostatic charge and locally creating an electric field associated with at least part of the surface of said implantable medical device upon application of a liquid to said surface.

In one embodiment, said electric field is used to attract specific biomolecules to said dielectric insulating layer, for example by electrophoresis. Preferably the biomolecules are selected from the group including preferably wherein the biomolecules are selected from the group including peptides, polypeptides, proteins, oligonucleotides, nucleic acids, RNA, antisense nucleic acids, small interfering RNA, ribozymes, genes, carbohydrates, angiogenic factors, cell cycle inhibitors and anti-restenosis agents. Preferably, said liquid is an electrolyte solution.

Preferably, said application of ions is onto part but not all of said dielectric insulating layer. It is not necessary to coat or completely cover the dielectric insulating layer with ions.

In one embodiment, said applied ions are capable of modifying the wettability of at least part of the surface of said implantable medical device.

The process may further comprise the production of an electrode pattern and/or topographic features on said dielectric insulating layer to which said ions are applied.

Preferably, the electrostatic charge is insufficient to initiate electrolysis.

In a preferred form, the dielectric insulating layer is provided on the surface of said implant intermediate a metallic part of said implant and a conductive fluid. The dielectric insulating layer may comprise a metal oxide layer, for example titanium oxide and/or may have a thickness in the range 1 nm-100 μm.

In one embodiment, the dielectric insulating layer includes a hydrophobic coating, for example a glass, ceramic or amorphous fluoropolymer coating.

In one embodiment, an aqueous solution of said ions is applied to said dielectric insulating layer by spraying, immersing or partially dipping said implant into said aqueous solution, the aqueous solution preferably including a volatile organic compound. Additionally, said aqueous solution may be a physiologically isotonic salt solution, preferably of 0.1-2.0% concentration.

The ions may be applied to said dielectric insulating layer by plasma vapour deposition.

Preferably, the ions include ions naturally found in bodily fluids. In one embodiment said ions include $Na^+$ or $K^+$ or $Mg^{2+}$ cations or $Cl^-$ or $PO_4^-$ anions.

Preferably, said applied ions have a thickness in the range 1 nm-100 μm.

The surface treatment process preferably further includes the step of drying the implant, for example by providing an elevated temperature, providing a desiccant, or placing the implant in an air or other gas stream.

In an alternative embodiment, said electrostatic charge is applied using an external alternating or direct current power supply, preferably a voltage in the range 10 mV-400V and/or wherein said electrostatic charge has a frequency in the range 0-20 kHz. Said electrostatic charge may have a sine, square, triangular or ramp waveform.

According to a second aspect of the invention there is provided an implantable medical device treated with the surface treatment process of any of the preceding paragraphs.

According to a third aspect of the invention there is provided an implantable medical device, preferably a dental implant, comprising a metallic layer on which is located a surface dielectric insulating layer, the dielectric insulating layer having ions thereon which are capable of forming an electrostatic charge and locally creating an electric field associated with at least part of the surface of said implantable medical device upon application of a liquid to said surface.

According to a fourth aspect of the invention there is provided a method of modifying the wettability of an implantable medical device comprising the steps of:

treating the implantable medical device with the process of any of the preceding paragraphs;

bringing the treated device into contact with a liquid whereby electrowetting is initiated.

Preferably electrowetting is initiated during implantation of said medical device. Alternatively, said medical device is implanted before electrowetting is initiated. Preferably said liquid is a bodily fluid, for example blood.

Further features of the invention are described in the appended claims.

BRIEF DESCRIPTION OF THE DRAWINGS

Preferred embodiments of the invention will now be more particularly described, by way of example only, with reference to the accompanying drawings in which.

DETAILED DESCRIPTION

Electrowetting is a process known in the field of digital microfluidics wherein the wetting properties of a hydrophobic surface can be modified using an externally applied electric field.

The electrowetting process is carried out by the production of suitable electrode patterns or topographic features on a substrate surface to which an electrostatic charge (charge or voltage) is applied causing variations in contact angle, changes in droplet shape, motion of fluids and an increase in overall surface wettability.

Such electrowetting enables the manipulation of fluids and the development of surfaces with controllable wettability. Electrowetting is very successful and contact angle variations of several tens of degrees can be routinely achieved.

In the field of implantable medical devices, including dental implants, external application of electrostatic charge may be impractical and/or undesirable. In one aspect therefore, the present invention relates to a surface treatment process for an implantable medical device which eliminates the need for externally-applied electrostatic charge.

Figure 1:
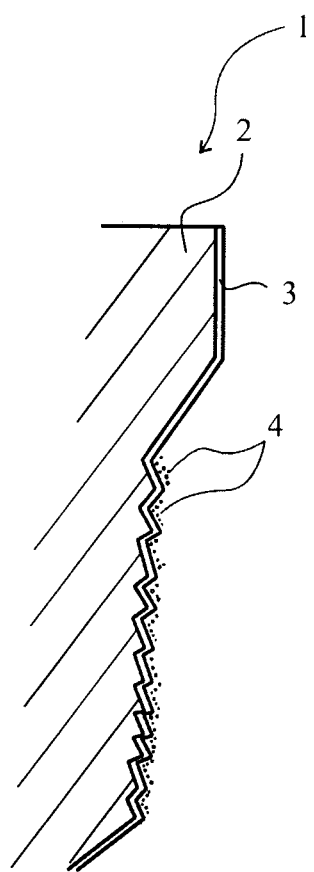
FIG. 1 is a schematic cross-sectional view of part of an implant treated with the process of the present invention.

FIG. 1 shows a schematic cross-section of part of an implantable medical device treated by the process described below. The implant 1 comprises a metallic or metallic alloy implant body 2 having an insulating dielectric layer 3 on the surface thereon. The implant body 2 may have a grit blasted and etched, or otherwise textured, surface. The dielectric layer 3 may be a metal oxide layer, for example such as titanium oxide which is commonly present on titanium medical implants. The dielectric layer may be inherently present on the surface (such as the metal oxide layer mentioned above) or created by a process step involving covering the implant body 2 with a thin hydrophobic top coating. Possible coatings include glasses, ceramics and amorphous fluoropolymers but others may be envisaged. The dielectric layer 3 may have a typical thickness in the range 1 nm-100 μm.

The next step in the process comprises treating the surface of the implant with ions. In one embodiment, the implant 1 is dipped or immersed in a solution of 1% $MgCl_2 6H_2O$ and agitated ultrasonically to ensure that no air bubbles are trapped in the roughened surface. Other suitable solutions for applying ions can be envisaged. For example, $Cl^-$ ions may be applied from a salt solution of NaCl.

The ions may be applied to the implant surface by spraying, immersing or partially or completely dipping the implant with an aqueous solution of an electrolyte. Plasma vapour deposition may alternatively be used. The solution may be electrolyte and water alone or a volatile organic compound may be added to enhance penetration. The concentration of the electrolyte may be variable. An example is a salt solution of 0.9% which is physiologically isotonic. In addition the amount of the organic compound may vary.

The wet implant is then dried, for example in an oven 5-15 minutes at 50-90° C., to drive off the water and leave the ions on the surface of the implant. Drying the implant can be carried out in a number of possible ways, for example: at an elevated temperature, in the presence of circulating air or a desiccant or in a gas or air stream. Drying is important to draw and deposit the ions into the pits, pores and capillary features of the surface.

The dried implant 1 now has ions 4 on the surface thereof. The ions 4 do not coat the surface of the implant in the conventional sense—the ions do not need to cover the entire surface of the implant. Application of ions particularly but not exclusively to the pits, pores and capillary features of the roughened part of the implant surface will create a local concentration of such ions. The thickness of the applied ions can be variable and may be in the range 1 nm-100 μm. The applied ions are not sufficient to perform any kind of protective coating function for the implant.

The ions on the surface of the treated implant are capable of forming an electrostatic charge thereon and locally creating an electric field associated with at least part of the surface of the implant upon application of a liquid to the surface, using a technique known as electrowetting on dielectric (EWOD).

If a voltage is applied between a metal surface electrode and an electrolyte solution, below the onset of electrolysis, an electric double layer builds up spontaneously at the solid-liquid interface consisting of charges on the metal surface and a cloud of oppositely charged counter ions on the liquid side of the interface. This leads to a desirable increase in wettability. Such electrowetting results in a decrease in contact angle and interfacial tension, increase in hydrophilicity and penetration of the surface topography overcoming bridging and capillary resistance.

In the treated implant, the implant body 2 comprises the electrode. The treated implant can be dipped, coated or otherwise put into contact with a liquid, for example a conductive electrolyte solution, in order to initiate EWOD. The liquid may be a non-conductive liquid which becomes conductive upon contact with the ions applied to the treated implant. The dielectric insulating layer 3 insulates the implant body electrode from the electrolyte solution that will be used in EWOD. In this EWOD configuration the electric double layer builds up at the dielectric-electrolyte interface.

The electrolyte solution used for EWOD may be a tissue fluid, blood, saline, or a carrier fluid carrying drugs, growth factors etc. The type or concentration of electrolyte solution does not have a significant influence on wettability. The solution may therefore be a single salt or combination of salts. Typical alkali metal cations such as $Na^+$ or $K^+$, with corresponding ions $Cl^-$, $PO_4^-$, are examples of many suitable. Such salt solutions may therefore comprise bodily tissue fluids.

In this way, local electrostatic forces may be generated by the treated implant upon contact with an electrolyte solution, without application of an external voltage, thus increasing the hydrophilicity of the surface and enabling liquids to fully penetrate the surface topography.

Figure 2:
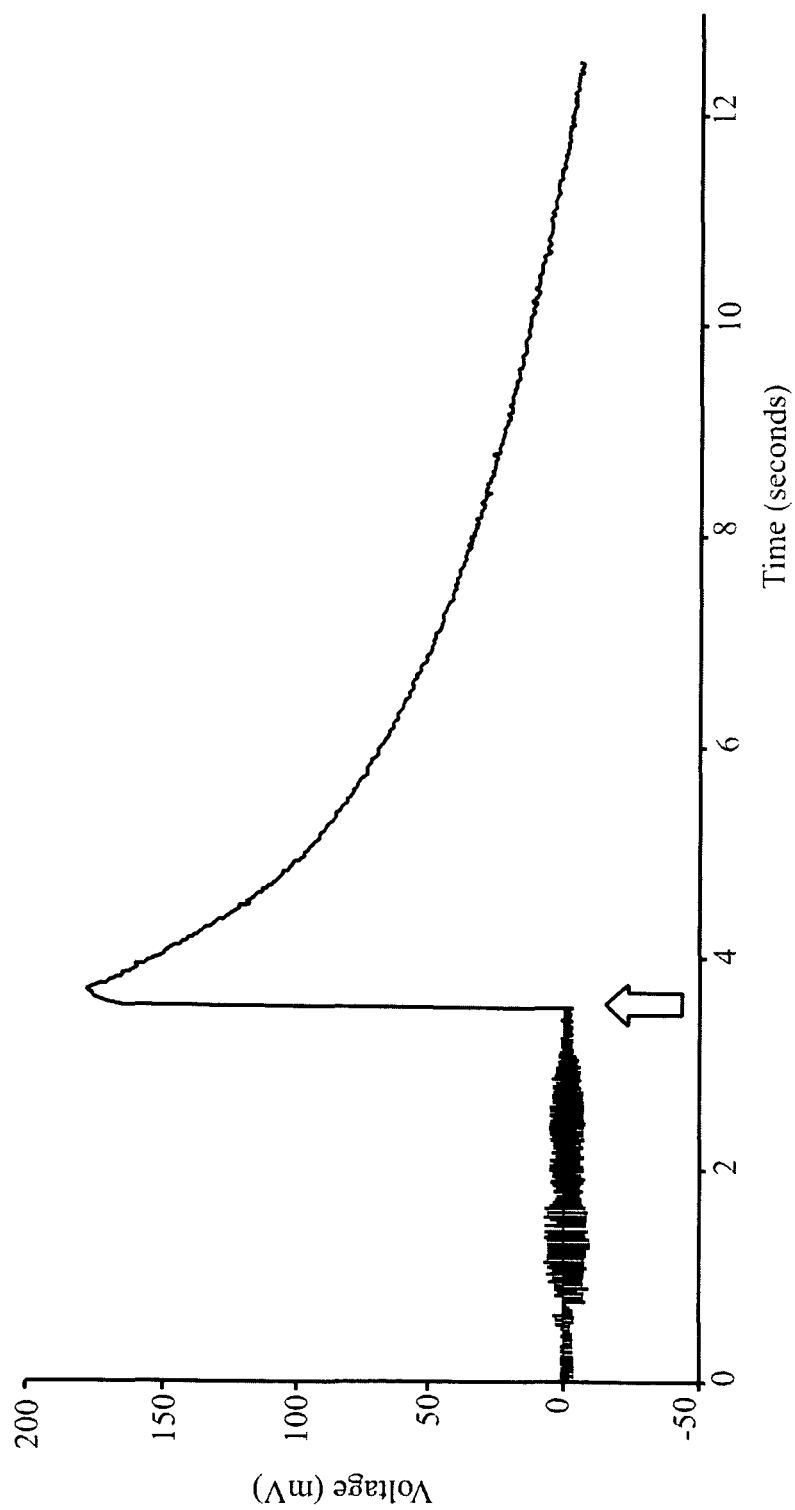
FIG. 2 is a graph indicating surface electric charge created at the surface of an implant treated with the process of the present invention.

FIG. 2 indicates the electrical charge that is produced when a treated implant is put into contact with a suitable liquid such as blood, tissue fluid or saline (arrow indicates the point in time at which the implant contacts the liquid). As the liquid is drawn into the implant surface, the voltage decreases with time.

If the ions applied to the implant surface are from salt $Na^+Cl^-$, a further advantage is that the salt will dissolve in the electrolyte solution which if bodily fluid will be entirely harmless being a constituent of such bodily or physiological fluid.

The EWOD process can be performed equally well in vitro as in vivo.

In one embodiment, the locally created electric field can be used to attract specific biomolecules to a surface. This can enable the preferential and increased level of bone formation in direct approximation to the surface. A non-exhaustive list of exemplary biomolecules includes: peptides, polypeptides, proteins, oligonucleotides, nucleic acids, RNA, antisense nucleic acids, small interfering RNA, ribozymes, genes, carbohydrates, angiogenic factors, cell cycle inhibitors and anti-restenosis agents.

In an alternative embodiment, a voltage applied to a circuit comprising a metallic implant surface with dielectric layer and suitable fluid (this may be tissue fluid, or a carrier fluid carrying drugs growth factors etc) will cause electrowetting resulting in a decrease in contact angle, increase in hydrophilicity and penetration of the surface topography overcoming bridging and capillary resistance. Alternatively, or in addition, the process can be used to attract specific biomolecules such as those listed above to a surface. The applied voltage may be from direct or alternating current and in the range 10 mV-400V and frequency 0-20 kHz and of waveform sine, square, triangular, ramp or arbitrary.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A surface treatment process for an implantable medical device including a surface dielectric insulating layer, the process comprising:
   applying ions from a solution of magnesium chloride to adhere magnesium ions onto an exterior of said surface dielectric insulating layer, and then drying the implant, said drying configured to draw and deposit the magnesium ions into pits, pores, and capillary features of the surface dielectric insulating layer, the deposited magnesium ions forming an electrostatic charge at the exterior of said surface dielectric insulating layer, and, in the absence of an externally applied voltage, the magnesium ions locally creating an electric field and dissolving upon application of a conductive fluid to said surface dielectric insulating layer during implantation, the electric field associated with at least part of a surface of said implantable medical device, and wherein said surface dielectric insulating layer is provided on the surface of the implantable medical device intermediate a metallic part of the implant and said conductive fluid.

2. The surface treatment process of claim 1 in which said electric field is associated with at least part of the surface of the implantable medical device and specific biomolecules upon application of the conductive fluid to said surface, wherein the biomolecules are selected from the group including peptides, polypeptides, proteins, oligonucleotides, nucleic acids, RNA, antisense nucleic acids, small interfering RNA, ribozymes, genes, carbohydrates, angiogenic factors, cell cycle inhibitors and anti-restenosis agents.

3. The surface treatment process of claim 1 in which said conductive fluid is an electrolyte solution.

4. The surface treatment process of claim 1 wherein said application of magnesium ions is onto part but not all of said dielectric insulating layer.

5. The surface treatment process of claim 1 wherein said application of magnesium ions is onto part but not all of said dielectric insulating layer and wherein said applied magnesium ions are configured to modify a wettability of at least part of the surface of said implantable medical device.

6. The surface treatment process of claim 1 further comprising:
producing an electrode pattern and/or topographic features on said surface dielectric insulating layer; and
selectively applying magnesium ions to the electrode pattern and/or topographic features but not to remaining portions of the surface dielectric insulating layer.

7. The surface treatment process of claim 1 wherein said electrostatic charge is formed so as to be insufficient to initiate electrolysis.

8. The surface treatment process of claim 1 wherein said surface dielectric insulating layer comprises a metal oxide layer.

9. The surface treatment process of claim 1 wherein said surface dielectric insulating layer has a thickness in the range of 1 nm-100 µm.

10. The surface treatment process of claim 1 wherein said surface dielectric insulating layer includes a hydrophobic coating selected from the group including a glass, a ceramic and an amorphous fluoropolymer coating.

11. The surface treatment process of claim 1 wherein an aqueous solution of said magnesium ions is applied to said surface dielectric insulating layer by one or more of spraying, immersing and partially dipping said implant into said aqueous solution.

12. The surface treatment process of claim 11 wherein said aqueous solution includes a volatile organic compound.

13. The surface treatment process of claim 11 wherein said aqueous solution is a physiologically isotonic salt solution.

14. The surface treatment process of claim 1 wherein said ions are applied to said surface dielectric insulating layer by plasma vapor deposition.

15. The surface treatment process of claim 1 wherein said applied ions have a thickness in the range of 1 nm-100 µm.

16. The surface treatment process of claim 1 wherein the step of drying the implant is performed by one or more of providing an elevated temperature, providing a desiccant, and placing the implant in an air or other gas stream.

17. The surface treatment process of claim 2 wherein an increased electrostatic charge is applied using an external power supply.

18. The surface treatment process of claim 17 wherein said increased electrostatic charge is a voltage in a range of 10 mV-400V.

19. The surface treatment process of claim 17 wherein said increased electrostatic charge is generated from direct current.

20. The surface treatment process of claim 17 wherein said increased electrostatic charge has a frequency in a range of 0-20 kHz.

21. The surface treatment process of claim 17 wherein said increased electrostatic charge has a sine, square, triangular or ramp waveform.

22. A method of modifying a wettability of an implantable medical device including a surface dielectric insulating layer, the method comprising the steps of:
applying ions from a solution of magnesium chloride to adhere magnesium ions onto an exterior of said surface dielectric insulating layer, and then
drying the implant, said drying configured to draw and deposit the magnesium ions into pits, pores, and capillary features of the surface dielectric insulating layer, the deposited magnesium ions forming an electrostatic charge at the exterior of said surface dielectric insulating layer, and,
in the absence of an externally applied voltage, the magnesium ions locally creating an electric field and dissolving upon application of a conductive fluid to said surface dielectric insulating layer during implantation, the electric field associated with at least part of a surface of said implantable medical device, and wherein
said surface dielectric insulating layer is provided on the surface of the implantable medical device intermediate a metallic part of the implant and said conductive fluid; and
bringing the implantable medical device into contact with the conductive fluid whereby electrowetting is initiated.

23. The method of claim 22 wherein electrowetting is initiated during implantation of said medical device.

24. The method of claim 22 wherein said medical device is implanted before electrowetting is initiated.

25. The method of claim 22 wherein said conductive fluid is a bodily fluid.

26. The method of claim 25 wherein said bodily fluid is blood.

27. The surface treatment process of claim 13, wherein said aqueous solution has a concentration of 0.1-2.0%.

28. The surface treatment process of claim 1 wherein an electric double layer builds up at an implant-conductive fluid interface.

29. The surface treatment process of claim 1 wherein the magnesium ions are applied from a 1% solution of $MgCl_2 6H_2O$.

30. The surface treatment process of claim 1, wherein application of the conductive fluid to the surface dielectric insulating layer during implantation initially results in generation of at least a 150 mV charge.

31. The surface treatment process of claim 30, wherein the charge generated upon application of the conductive fluid to the surface dielectric insulating layer decays over time as the conductive fluid is drawn into the pits, pores, and capillary features of the surface dielectric insulating layer.

* * * * *